United States Patent
Wildgoose et al.

[11] Patent Number: 5,690,636
[45] Date of Patent: Nov. 25, 1997

[54] PUNCH SYSTEM FOR TIBIAL PROSTHESIS

[75] Inventors: Sarah Anne Wildgoose, Smithfield, R.I.; Ernest Quintanilha, Norton; Diana F. McCue, Pocasset, both of Mass.

[73] Assignee: Johnson & Johnson Professional, Inc., Raynham, Mass.

[21] Appl. No.: 576,746

[22] Filed: Dec. 21, 1995

[51] Int. Cl.$^6$ ............................................. A61B 17/56
[52] U.S. Cl. ........................ 606/88; 606/100; 606/184; 623/20
[58] Field of Search ................... 606/79, 80, 85, 606/86, 87, 88, 89, 96, 99, 100, 184; 623/20

[56] References Cited

U.S. PATENT DOCUMENTS

| | | | |
|---|---|---|---|
| 4,825,857 | 5/1989 | Kenna | 128/92 VW |
| 4,921,493 | 5/1990 | Webb, Jr. et al. | 606/85 |
| 5,108,402 | 4/1992 | Chin | 606/93 |
| 5,250,050 | 10/1993 | Poggie et al. | 606/79 |
| 5,282,866 | 2/1994 | Cohen et al. | 623/20 |
| 5,356,414 | 10/1994 | Cohen et al. | 606/88 |
| 5,443,471 | 8/1995 | Swajger | 606/99 |
| 5,499,984 | 3/1996 | Steiner et al. | 606/80 |
| 5,499,985 | 3/1996 | Hein et al. | 606/99 |

FOREIGN PATENT DOCUMENTS

| | | |
|---|---|---|
| 0 474 320 A1 | 3/1992 | European Pat. Off. . |
| 0 556 998 A1 | 8/1993 | European Pat. Off. . |

*Primary Examiner*—Michael Buiz
*Assistant Examiner*—David O. Reip

[57] ABSTRACT

A punch system is provided for preparing a keel cavity in a tibial bone for implantation of a prosthesis. The system provides a modular punch system providing a logical step-to-step approach to cutting, punching, and/or forming the tibial bone. The system of a preferred embodiment includes a quick release punch guide for attaching to a tibial tray trial component of a surgical instrument system for implanting artificial knees, and a universal quick release handle for attaching or detaching a punch from a handle or slap hammer.

20 Claims, 5 Drawing Sheets

PUNCH SYSTEM FOR TIBIAL PROSTHESIS

FIELD OF THE INVENTION

The present invention relates to a system for preparing a keel cavity in the tibial bone for implantation of a tibial prosthesis.

BACKGROUND OF THE INVENTION

During knee replacement surgery a surgeon prepares, among other things, the tibial bone to receive a tibial tray (and insert) for implantation. A surgeon uses a tibial tray trial to determine the tibial implant size, to ensure proper alignment and tibial implant thickness, and to make the appropriate cuts or recesses in the bone for receipt of the tibial tray implant.

A variety of implant features and types of tibial trays require different tools and techniques to prepare the tibial bone for implantation. Standard non-cemented tibial implants require a different cut, shape and length than a cemented implant. Similarly a modular type implant requires a different bone recess size and type for both its cemented and non-cemented versions.

Typically, during tibial preparation procedures, a tibial tray trial is selected to correspond with the implant type. Accordingly, the tibial tray trial will have an opening to accommodate the appropriate punch and/or drill shape for that particular implant type. A punch, and, if necessary, a drill is used to form a recess in the tibial bone into which the keel of the tibial implant is to be placed. Typically the punch has a handle with a punching end piece, and a guide for protecting and/or receiving the end piece, located on the end of the handle. Each type of punch has a different end piece and guide. Thus, for each type of implant, a different handle, end piece, and punch guide is required. Furthermore, a slap hammer may be used instead of a handle, for example, in situations where it may be desirable to extract the punch, thus for each type of punch, a different slap hammer would be required.

It is, therefore, desirable to provide a tibial preparation system in which less pieces are required and which will save money and space in the operating room.

SUMMARY OF THE INVENTION

Accordingly, the present invention includes a modular punch system providing a logical step-to-step approach to cutting, punching and/or forming the tibial bone in preparation for an implant.

One feature of the present invention provides a universal connect/disconnect mechanism for a universal handle or slap hammer. A preferred embodiment includes a quick-release mechanism located at the distal end of the handle or slap hammer. The quick-release mechanism is adapted to attach and detach from modular components of an implant instrument system including punches, impactors, extractors, etc.

In a preferred embodiment, the handle and slap hammer attach firmly to the modular components, with the quick-release mechanism comprising a captive spring loaded sliding pin that locks the handle or slap hammer into position. The sliding pin is attached to a knob which when retracted allows the connecting portion to engage with a mating part of a punch, impactor, or any similar modular component of the system. A T-shaped slot of the modular component mating portion receives the end of the universal handle or slap hammer. When the knob of the handle or slap hammer is released, the pin extends into the hole in the modular component thereby preventing the end of the universal handle or slap hammer from disengaging from the modular component. The handle or slap hammer is disengaged in a similar manner by retracting the knob, drawing the sliding pin back into the body of the handle/slap hammer and sliding the quick release mechanism out of the T-shaped slot. The handle or slap hammer may be connected or disconnected using one hand, leaving the other hand free for other purposes.

Another feature of the invention provides separate, modular punch guides adapted to be removably attached to various tibial tray trials. Each punch guide is arranged to receive a predetermined set of punches and drills which are capable of forming the appropriate tibial impressions for a particular implant type and size. In a preferred embodiment, the punch guide may be attached to a tray trial by a quick-release mechanism consisting of a captive, spring-loaded sliding bolt which engages to a mating part of a tray trial. The sliding bolt is retracted by the thumb on a release button which allows quick attachment and detachment from the mating component. The punch guides can be removed or attached using one hand, leaving the other hand free for other purposes.

DETAILED DESCRIPTION OF THE DRAWINGS

DETAILED DESCRIPTION OF THE INVENTION

Figure 1:
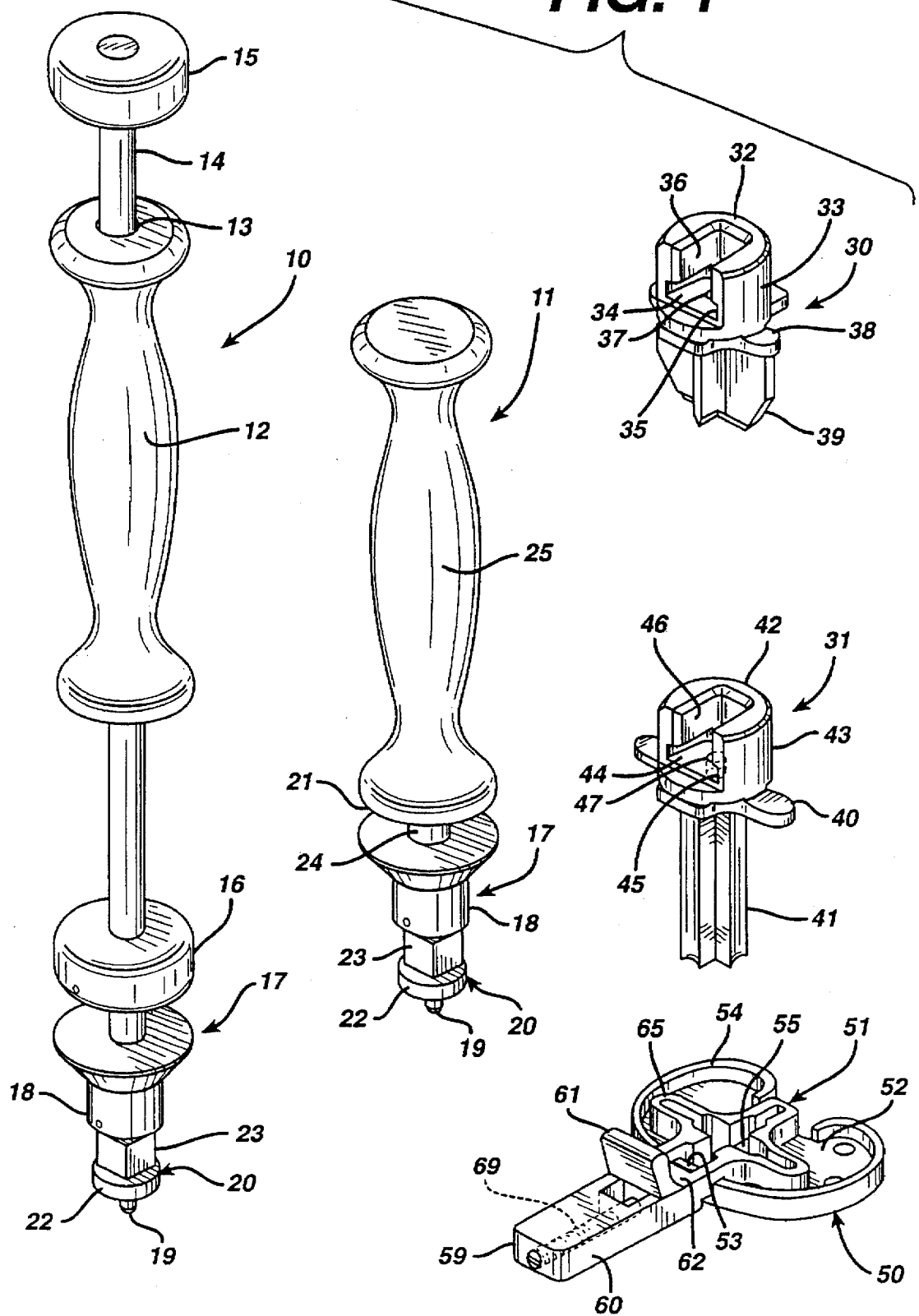
FIG. 1 illustrates a system of the present invention comprising the standard tibial keel punch system.
Figure 5:
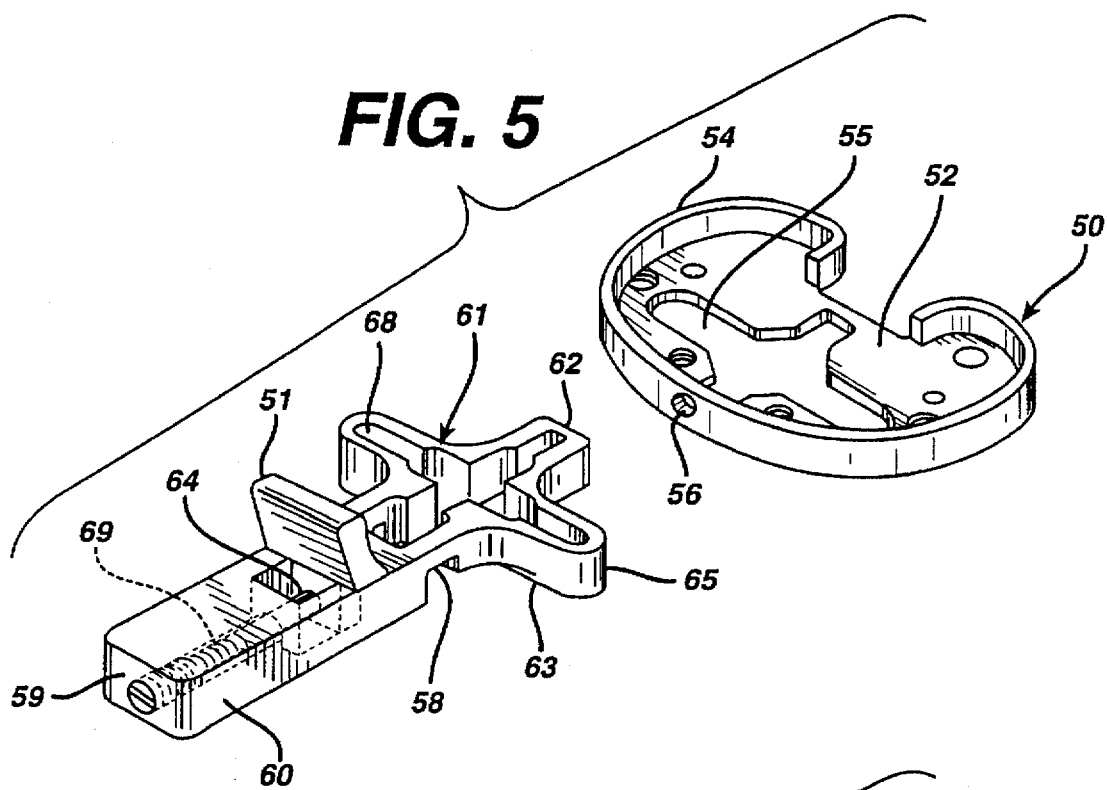
FIG. 5 illustrates an exploded perspective view of the punch guide in use with tray trial of FIG. 1.
Figure 6:
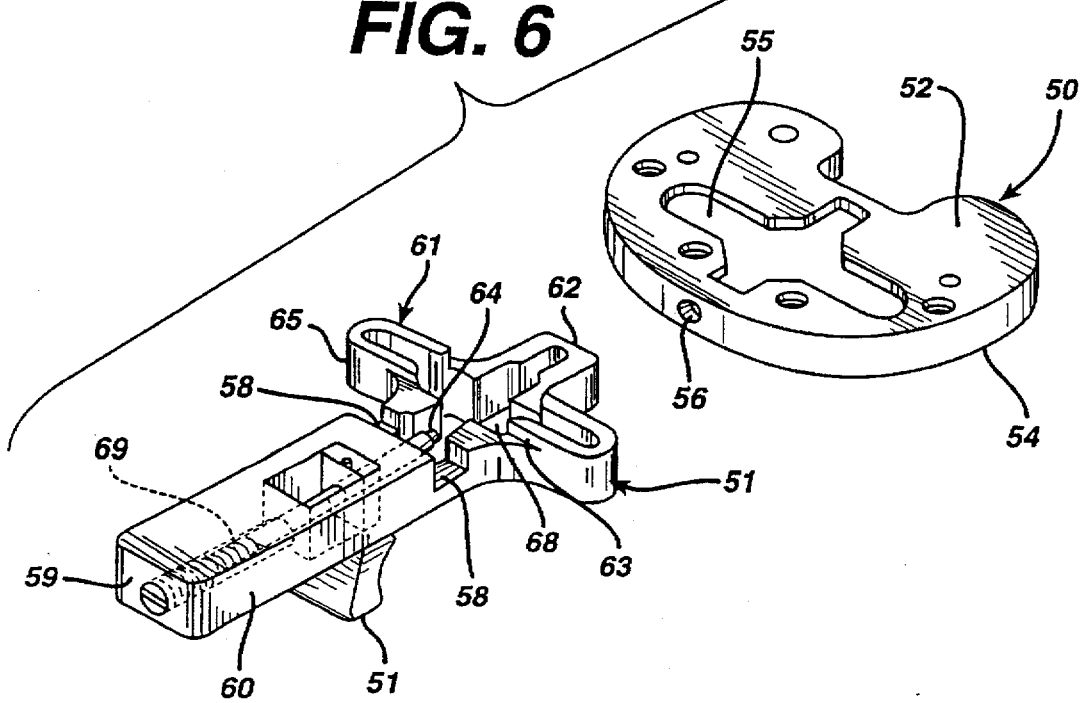
FIG. 6 illustrates a bottom exploded perspective view of the punch guide and tray trial of FIG. 5.

Referring now to FIG. 1, a standard tibial keel punch system of the present invention is illustrated. FIGS. 5 and 6 illustrate a punch and tray trial of FIG. 1 in use together. The standard system includes components for preparing a tibial bone for a standard cemented or non-cemented implant. The system comprises a slap hammer 10, a handle 11, a standard non-cemented punch 30, a standard cement punch 31, a tray trial 50, and a standard punch guide 51.

The slap hammer 10 includes a sliding handle 12 having an opening 13 through which the stem 14 of the slap hammer extends. The handle 12 is arranged to slide up and down between stops 15, 16. The slap hammer 10 further comprises a quick-release mechanism 17 extending distally from the stem 14. The quick-release mechanism 17 comprises a knob 18, a pin 19, and a universal connecting portion 20 having a T-shaped longitudinal cross-section coupled to the stem 14 and located at the distal end of the slap hammer 10. The pin 19, coupled to the knob 18, extends distally of knob 18 through the connecting member 20. The knob 18 is spring-loaded in a distal direction and is adapted to move between stop 16 and connecting member 20. When the knob 18 is moved in a proximal direction, the pin 19 is retracted into the connecting member 20. When the knob 18 is released, the spring-loaded bias of the knob 18 causes the knob 18 and pin 19 to move in a distal direction so that the pin 19 extends distally from the connecting member 20.

The handle 11 comprises a handle portion 25, a stem 24, and a quick release mechanism 17 located at the distal end of the stem 24. The quick release mechanism 17 comprises a knob 18, a pin 19 coupled to the knob 18, and connecting member 20 coupled to the stem 24 through the knob 18. The quick release mechanism 17 is the same device as the quick-release mechanism 17 on the slap hammer 10. The knob 18 is spring-loaded in a distal direction and is adapted to move between the distal end 21 of the handle portion 25 and connecting member 20. When the knob 18 is moved in a proximal direction, the pin 19 is retracted into the connecting member 20. When the knob 18 is released, the spring-loaded bias of the knob 18 causes the knob 18 and pin 19 to move in a distal direction so that the pin 19 extends distally from the connecting member 20.

The connecting member 20, included with both the slap hammer 10 and handle 11, is arranged to couple with the non-cemented standard punch 30 and the standard cement punch 31. The standard non-cemented punch 30 is used to form a shape in the tibia to receive standard or cruciform tibial keel. The standard cement punch 31 is arranged to form an extra recess in the tibia to provide additional space for cement around a standard or cruciform keel after the standard non-cemented punch 30 is used.

The non-cemented punch 30 comprises a universal connector 32 having a cylindrical member 33 with an opening 34 in its outer circumference for receiving the connecting member 20. The opening 34 includes a groove 35 for receiving a lower portion 22 of the connecting member 20, and a narrower opening 36 for receiving an upper portion 23 of the connecting member 20. The non-cemented punch 30 finally comprises an opening 37 located on the bottom of the groove 35 for receiving the pin 19 of the connecting member 20 to lock the connecting member 20 to the non-cemented punch 30. The connector 32 is coupled to the base 38 of the non-cemented punch 30. The base 38 has an end piece 39 which has appropriate shape for reaming the tibial bone to receive a similarly shaped keel of a standard keel implant.

The standard cement punch 31 includes a universal connector 42 comprising a cylindrical member 43 with an opening 44 in its outer circumference. The opening 44 includes a groove 45 for receiving the lower portion 22 of the connecting member 20; narrower opening 46 for receiving the upper portion 23 of the connecting member 20; and an opening 47 for receiving the pin 19. The universal connector 42 operates in a similar manner as the connector 32 of the non-cemented punch 30 as described above. The connector 42 is coupled to the base 40 of the cement punch 31. Cement punch 31 includes an end piece 41 extending distally from the base 40 and having a size and length corresponding to the desired formed recess for a standard keel tibial implant, and cemented application, i.e., typically longer and narrower than the non-cemented punch.

The standard tibial keel punch system further comprises a tray trial 50 and a standard punch guide or cruciform 51.

The tibial tray trial 50 comprises a plate portion 52, a rim 54 around the outer circumference of the plate portion 52, a mating portion 53 of the rim 54, and a punch opening 55 formed in the tibial tray trial plate 52. The mating portion 53 includes a hole 56 for receiving a sliding bolt 64 of the punch guide 51. The hole 56 extends through the rim 54 of the mating portion 53.

The punch guide 51 includes a handle portion 60 having a handle end 59, punch end 62, and a release button 61 slidable in a direction from the handle end 59 to the punch end 62 and visa versa. The punch guide 51 further comprises a captive sliding bolt 64, i.e., contained within the handle 60. The sliding bolt 64 is coupled to the button 61. The bolt 64 is spring-loaded in direction from handle to punch by way of spring 69. The bolt 64 extends from the punch end 62 when the button 61 is extended, and retracts into the punch end 62 when the button 61 is retracted. The punch end 62 of the handle 60 is coupled to a guide portion 65. The punch guide 51 includes recessed surfaces 58 at the punch end 62 for receiving the mating portion 53 of the rim 54. The guide portion 65 includes posterior surfaces 63 and an opening 68 for receiving a punch.

In use, a user controls the attachment and detachment of the punch guide 51 to the tray trial 50, using the release button 61. The release button 61 is pulled in a proximal direction which retracts the bolt 64 into the handle 60. The punch guide 51 is placed over the trial 50 so that the opening 68 of the guide portion 65 of the punch guide 51 is aligned with the opening 55 of the tray trial 50, and so that the recessed surfaces 58 lo clear the rim 54 allowing the guide portion 65 to sit on top of the plate portion 52 of the tray 50 in proper alignment. Posterior surfaces 63 of the guide portion 65 prevent anterior-posterior movement of the punch guide 51 by engaging with the rim 54. The bolt 64 is aligned with the opening 56 when the punch guide 51 is placed over the tray trial 50. Thus, when the user releases the release button 61, the spring 69 causes the bolt 64 to move through the hole 56 in the mating portion 53. The locked bolt 64 prevents side to side movement, posterior-anterior movement, and removal (i.e., up and out movement) of the punch guide 51.

In a knee replacement procedure, the tibial tray trial 50 is used as a template to select the appropriate size tibial prosthesis for implantation. The trial 50 is placed on the tibia bone. The surgeon evaluates the alignment and necessary thickness of the tibial and femoral trial implants. Once appropriate alignment, and tibial tray size and location is determined, the tibial bone may be reamed. The standard cruciform punch guide 51 is inserted and locked into the tibial tray trial 50 as described above. The opening 68 of the guide portion 65 of the punch guide 51 is then aligned up over the punch guide opening 55 of the tray trial 50. The opening 55 of the tray trial is preferably the same shape as or is larger than the opening 68 of the guide portion 65 of the punch guide 51.

The guide portion opening 68 is shaped to receive either the standard cement punch cutting portion 41 or the standard non-cemented punch cutting portion 39. The punch 30 is selected and is attached with the connecting portion 20 to either the slap hammer 10 or the handle 11. The punch 30 is inserted through the opening 68 in punch guide 51 and opening 55 in tray trial 50. The user holds the handle 11 and applies pressure to form the recess in the tibia. Alternatively, if the slap hammer 10 is used, the user holds the handle portion 12 and moves it up and down, along the stem 14 to apply pressure, particularly as the handle portion 12 hits the stop 16, to form the recess in the tibia. The slap hammer 10 may then be used to extract the punch 30 by applying more pressure as the handle portion 12 hits the stop 15. If a cemented implant is to be used, the process is repeated using slap hammer 10 or handle 11, and the standard cemented punch 31 to form a recess for receiving cement.

Figure 2:
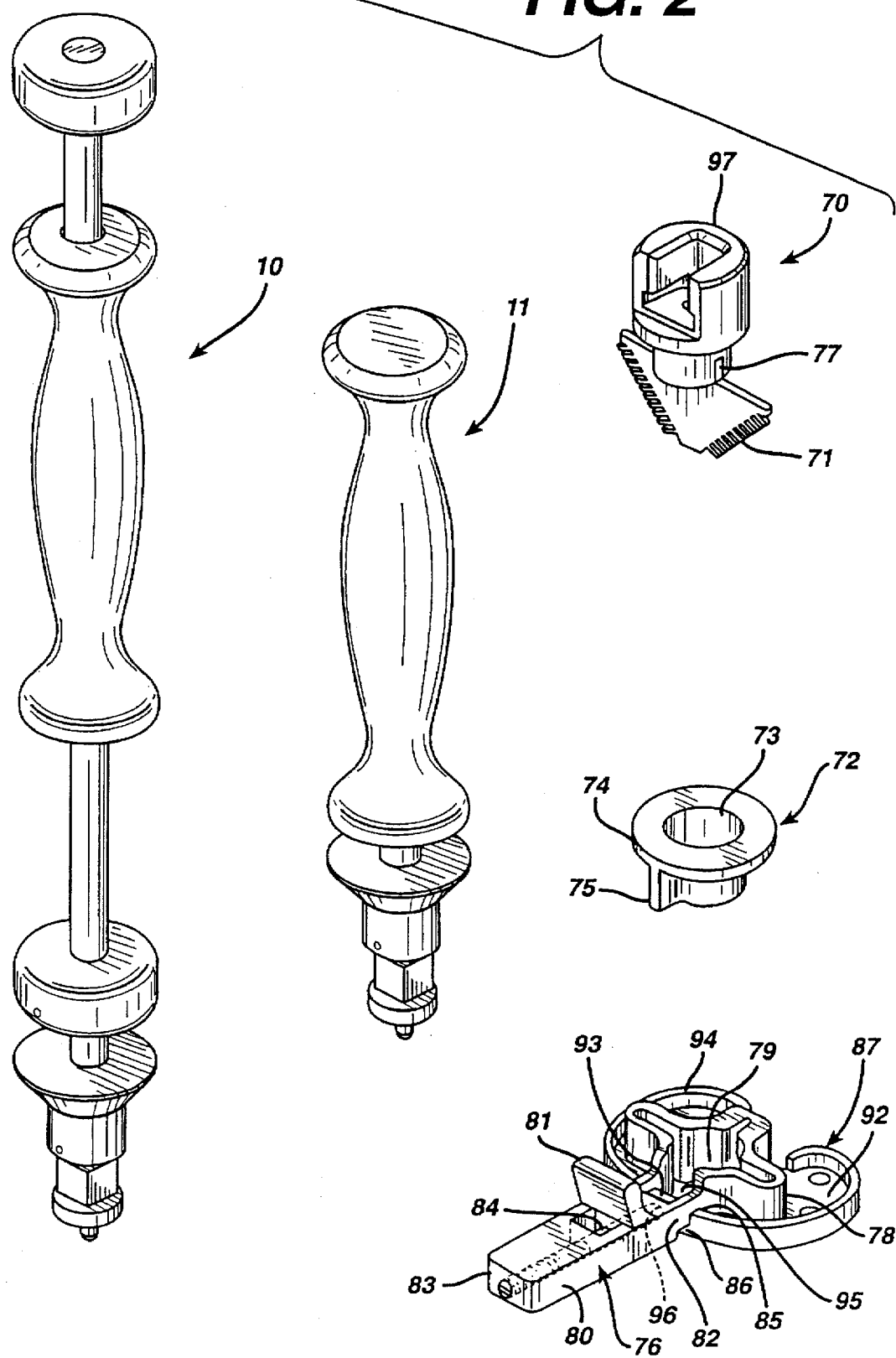
FIG. 2 illustrates a system of the present invention comprising a modular non-cemented tibial keel punch system.

FIG. 2 illustrates a modular non-cemented tibial keel punch system of the present invention. The system comprises the slap hammer 10 and the handle 11 as well as tray trial 87. The system further comprises a modular non-cemented punch 70, a drill bushing 72, and a modular non-cemented punch guide 76.

The modular non-cemented punch 70 comprises a universal connecting piece 97, which operates in the same manner as the universal connecting piece 32 of FIG. 1 to couple the slap hammer 10 or handle 11 to the punch 70. The modular non-cemented punch 70 includes a end piece 71 coupled to a base 77 which is coupled to the universal connecting piece 97. The end piece 71 is used to form a recess in the tibia.

The drill bushing 72 comprises a flange 74, a guide piece 75 extending from the flange 74, and an opening 73 extending through the flange 74 and guide piece 75. The opening 73 is used to receive a drill used to drill a hole in the tibia. The guide piece 75 prevents rotation within the punch guide 76 during drilling.

The handle portion 80 includes a handle end 83, punch end 82 and release button 81 slidable in a direction from the handle end 83 to the punch end 82 and visa versa. The punch end 82 further comprises a captive sliding bolt 84 coupled to button 81, spring loaded in a handle to punch direction, and retractable to a position within the handle portion 80. The punch end 82 also comprises surfaces 86 for clearing the rim 94 of a mating portion 93 of the tray trial 87. The handle portion 80 also includes a guide portion 78 coupled to its punch end 82. The guide portion 78 has a opening 79 shaped to receive the drill bushing 72 or punch 70 and posterior surfaces 85 for preventing anterior-posterior movement of the punch guide 76.

The tray trial 87 comprises a plate portion 92, a rim 94 around the outer circumference of the plate portion 92, a mating portion 93 of the rim 94 and a punch opening 95 formed in the plate portion 92. The mating portion 93 includes a hole 96 for receiving sliding bolt 84 of the punch guide 76. The mating portion 93 couples with the punch end 82 in a manner like that of the mating portion 53 and punch end 62 of FIG. 1.

In use the tibia trial is sized, selected, and placed on the tibia bone as described above with respect to the standard tibial trial. The punch guide 76 is attached to the trial 87 in a manner similar to the punch guide 51 and tray trial 50 of FIG. 1. The drill bushing 72 is placed in the opening 79 of the punch guide 76. A hole of a pre-determined depth is drilled in the tibia. The drill bushing 72 is removed and the punch 70 is attached to the slap hammer 10 or handle 11. The punch 70 is used to further shape the tibial bone in a manner as described above with respect to the standard tibial trial system.

Figure 3:
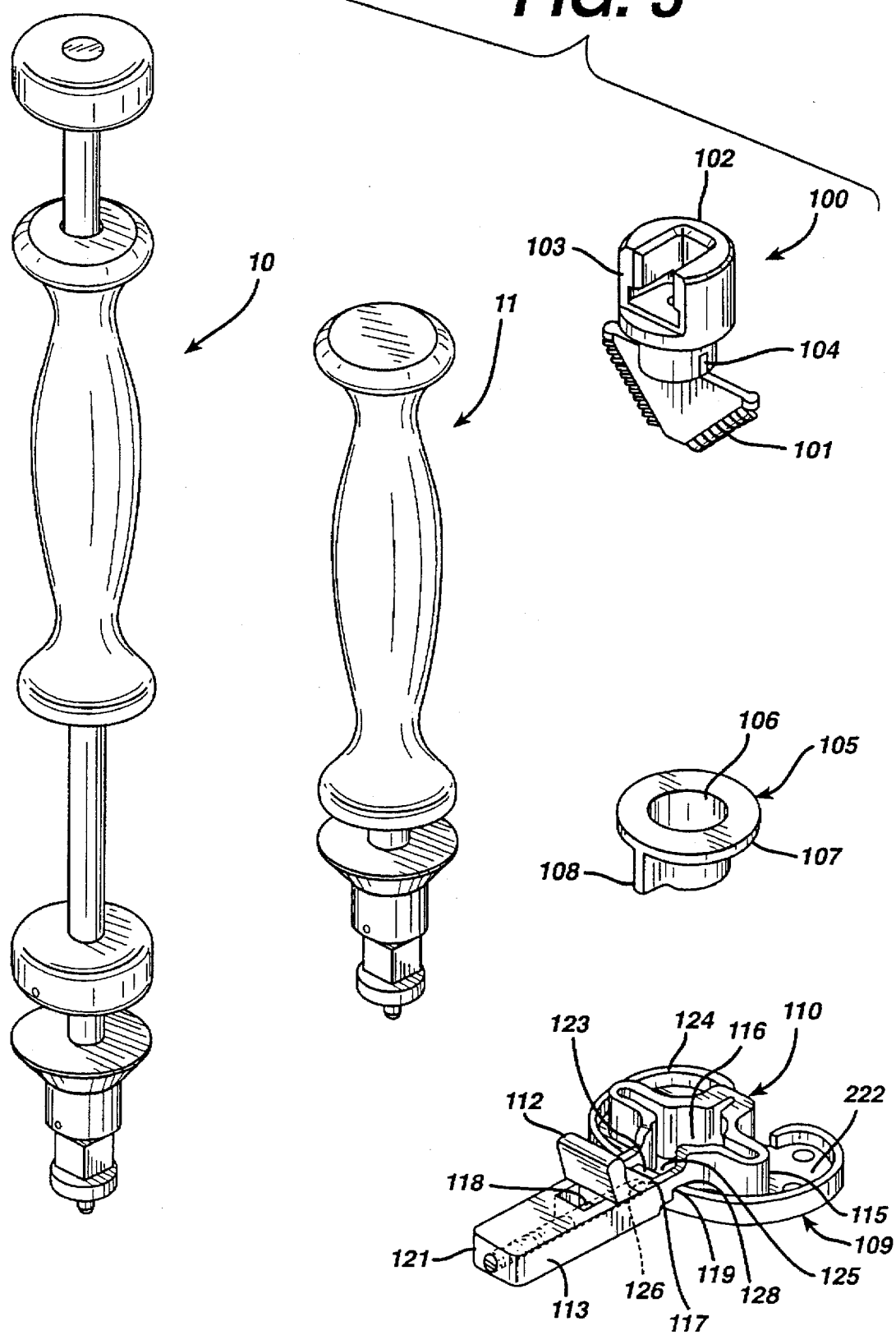
FIG. 3 illustrates a system of the invention comprising a modular cemented tibial keel punch system.

FIG. 3 illustrates a modular cemented tibial keel punch system of the present invention. The system comprises the slap hammer 10 and handle 11, and tray trial 109 similar to the trials illustrated in FIGS. 1 and 2. The system further comprises a modular cemented punch 100, a drill bushing 105, and a modular cemented punch guide 110. The drill bushing 105 is similar to the drill bushing 72 illustrated in FIG. 2, but having a size appropriate for receiving the appropriate drill used in preparation for a modular cemented implant. The drill bushing 105 comprises a flange 107, a guide piece 108 extending from the flange 107, and an opening 106 for receiving a drill, extending through the flange 107 and guide piece 108. The universal connecting piece 103 operates in the same manner as the universal connecting pieces 32 and 97 of FIGS. 1 and 2, to couple the slap hammer 10 or handle 11 to the punch 100. The modular cemented punch 100 includes an end piece 101 coupled to a base 104 which is coupled to a universal connecting piece 103. The end piece 101 is used to form a recess in the tibia.

The punch guide has a handle portion 113 including a handle end 121, punch end 117 and release button 112 slidable in a direction from the handle end 121 to the punch end 117 and visa versa. The punch end 117 further comprises a captive sliding bolt 118 coupled to button 112, spring loaded in a handle to punch direction, and retractable to a position within the handle 113. The punch end 117 also comprises a guide portion 115 coupled to the punch end 117. The guide portion 115 comprises surfaces 119 for clearing a mating portion 123 of the rim 124 and posterior surfaces 128 for preventing anterior-posterior movement of the punch guide 110. The handle portion 113 includes a guide portion 115 coupled to its punch end 117. The guide portion 115 has a opening 116 shaped to receive the drill bushing 105 or punch 100. The modular cemented punch guide 129 attaches to the tray trial 109 in the same way that the punch guides 51, 76 attach to tray trials 50, 87 as described in FIGS. 1 and 2.

The tray trial 109 comprises a plate portion 122, a rim 124 around the outer circumference of the plate portion 122, a mating portion 123 of the rim 124 and a punch opening 125 formed in the plate portion 122. The mating portion 123 includes a hole (not shown) for receiving sliding bolt 118 of the punch guide 110. The mating portion 123 couples with the punch end 117 in a manner like that of the mating portion 53 and punch end 62 of FIG. 1.

In use the tibia trial is sized, selected, and placed on the tibia bone as described above with respect to the standard tibial trial system. The punch guide 110 is attached to the trial 109 in a manner similar to the punch guides 51, 76 and tray trials 50, 87 of FIGS. 1 and 2 respectively. The drill bushing 105 is placed in the opening 116 of the punch guide 110. A hole of a pre-determined depth is drilled in the tibia. The drill bushing 105 is removed and the punch 100 is attached to the slap hammer 10 or handle 11. The punch 100 is used to further form a shape in the tibial bone in a manner as described above with respect to the system described with reference to FIG. 2.

Figure 4:
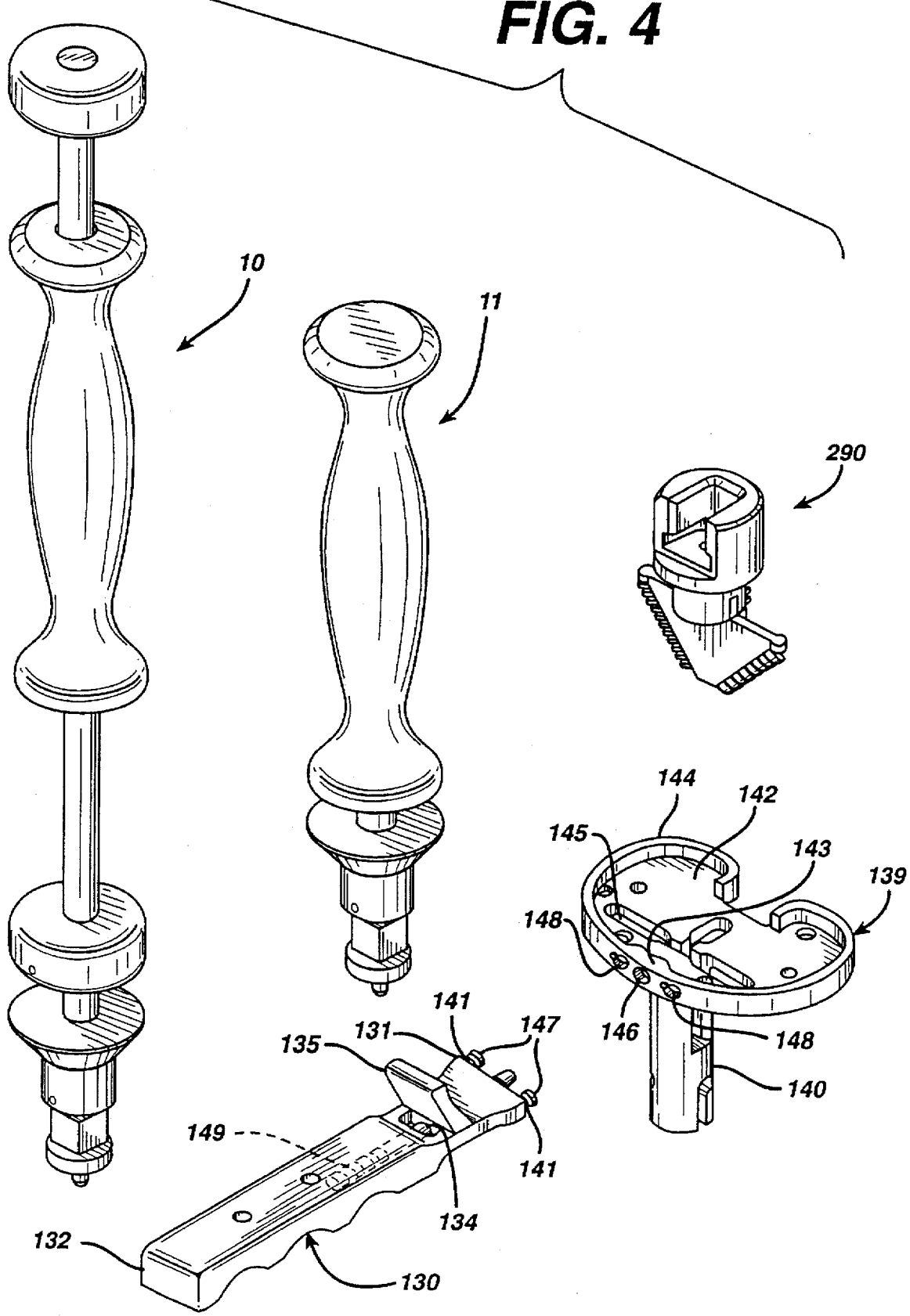
FIG. 4 illustrates a system of the invention comprising a revision tibial keel punch system.

Referring to FIG. 4, the revision tibial keel punch system is illustrated comprising a slap hammer 10 and handle 11 as illustrated in FIGS. 1 through 3; a tray trial 139 with stem 137; and a tibial tray trial alignment handle 130.

The alignment handle 130 is illustrated having a handle end 132 and a connecting end 131. The alignment handle 130 includes a release button 135 slidable in a direction from the connecting end to the handle end, i.e., posterior to anterior, and visa versa. The button 135 is coupled to a sliding bolt 134 which is captive, i.e., contained within the alignment handle 130. The bolt 134 is spring-loaded in a direction from anterior to posterior (maybe show spring). The connecting end 131 of the handle 130 comprises connecting bolts 141 having cylindrical heads 147 on the end of the bolts 141. The heads 147 have a greater circumference than the circumference of the bolts 141.

The tibial tray trial 139 comprises a plate portion 142; a rim 144 around the outer circumference of the plate 142; a mating portion 143 of the rim 144; a stem 137 extending distally from the plate 142; and a punch guide opening 145 in the plate 142.

The mating portion 143 includes a hole 146 for receiving a sliding bolt 134 of the handle 130 and openings 148 for receiving connecting bolts 141 of the handle 130. Openings 146, 148 extend through the rim 144 of the mating portion 143. Openings 148 each include a first portion on one transverse side of the opening 148 having a first radius and a second portion on the opposite transverse side having a second radius smaller than the first radius.

The bolt 134 extends from the connecting end 131 when the button 135 is extended, and retracts into the handle end 132 when the button 135 is retracted. The bolts 141 are slid into openings 148, the first radii of the openings 148 being large enough to accommodate the larger circumference of heads 147 of the bolts 141 which, when, inserted into the openings 148, extend beyond rim 144. The handle 130 is then moved in a direction towards the second portion of the opening 148 into a locked position. The second radii are too small to permit passage of the larger circumference heads 147 but large enough to receive the smaller circumference bolts 141.

The alignment handle 130 is used to place and remove the tray trial 149 on and from the tibia. A user controls the attachment and detachment of the handle 130 to the tray trial 149, using the release button 135. The release button 135 is pulled in an anterior direction which retracts the bolt 134 into the handle 130. The heads 147 of the bolts 141 on the distal end 132 of the handle 130 are inserted into openings 148 and moved to the locked position as described above. The bolt 134 is aligned with the opening 146 when the handle 130 is in the second or locked position. Thus, when the user releases the release button 135, the spring 149 causes the bolt 134 to move through the hole 146 in the mating portion 143. The locked bolt 134 prevents side to side movement of the handle 130 and the heads 147 prevent the bolts 141 from pulling out of holes 148.

The revision tray trial 139 is different from the tray trials previously described herein in that the trial includes a stem 137 necessary for revision tibial implants where the tibia has been previously cut. Also, the revision tray trial 139 includes the punch guide opening 145 directly in the plate 142 of the tray trial 139. Thus, no attachable punch guide is used for guiding the punch 136 into the tibial bone.

It is noted that the systems illustrated in FIGS. 1–3 may also include an alignment handle as described with respect to the revision trial illustrated in FIG. 4.

Although the present invention is described with respect to particular embodiments and features and uses, numerous variations or equivalents are possible without taking away from the spirit or scope of the claimed invention.

We claim:

1. A punch system for preparing a tibial bone for a prosthetic implant, said punch system comprising:
   a tray trial for performing a trial reduction in a knee replacement surgery, said tray trial having a proximal end with a circumferential rim, an opening for receiving a punch and a mating portion for coupling with a punch guide; and
   a punch guide comprising:
      a handle portion;
      a guiding portion coupled to the handle portion, said guiding portion including an opening for receiving a punch; and
   a locking mechanism comprising:
      a coupling portion for engaging with said mating portion of said tray trial;
      a quick release for disengaging said coupling portion from said mating portion, said quick release further comprising a spring-loaded release button having a coupling position and a release position, said button being slidable from said coupling position to said release position and being biased towards said coupling position;
      wherein said opening in said tibial tray is substantially aligned with said opening in said guide portion of said punch guide when said coupling portion is engaged with said mating portion to permit the insertion of a punch through said openings.

2. The punch system of claim 1 further comprising a punch coupled to a handle portion wherein said handle portion is arranged to apply a force to said punch.

3. The punch system of claim 2 wherein said punch comprises an end piece coupled to a universal connecting portion and wherein said handle piece comprises a connector adapted to fit to said connecting piece to removably couple said handle portion to said punch.

4. The punch system of claim 3 wherein said hand piece further comprises a spring-loaded release knob having a coupling position and a release position;
   wherein said knob is slidable from said coupling position to said release position;
   wherein said knob is biased towards said coupling position; and
   wherein said knob is coupled to said connector.

5. The punch system of claim 4 wherein said connector comprises a sliding bolt; and wherein said universal connecting portion comprises an opening for receiving said bolt.

6. The punch system of claim 5 wherein said universal connecting portion includes a locking portion adapted to engage said connector in a locked, coupled position with said universal connecting portion when said sliding bolt is located in said opening.

7. The system of claim 2 wherein said hand piece comprises a stationary handle.

8. The system of claim 2 wherein said hand piece comprises a slap hammer.

9. The system of claim 2 further comprising a plurality of punches adapted to be inserted through said opening in said punch guide and through said opening in said tray trial.

10. The system of claim 9 wherein said plurality of punches comprises a standard non-cemented punch.

11. The system of claim 10 wherein said plurality of punches further comprises a standard cemented punch.

12. The system of claim 2 wherein said punch comprises a modular non-cemented punch.

13. The system of claim 2 wherein said punch comprises a modular cemented punch.

14. The system of claim 13 further comprising a drill bushing having a dimension enabling said drill bushing to fit in said punch guide to receive and guide a drill bit for drilling into the tibia.

15. The punch system of claim 1 wherein said quick release comprises a sliding bolt and wherein said mating portion comprises an opening for receiving said sliding bolt.

16. The punch system of claim 15 wherein said mating portion further comprises a locking portion adapted to engage and lock said punch when said button is in said coupling position.

17. The punch system of claim 1 further comprising an alignment handle comprising:
   a body having a connecting end portion;
   a connecting member located at said connecting end portion, said connecting member having a first position whereby said connecting member may be coupled with said mating portion of said tray, and a second position whereby said connecting member is released from the mating portion of said tibial tray trial, wherein said connecting member is biased towards said first position; and
   a hand actuable quick-release button located on said body and coupled to said connecting member, said button actuable to move said connecting member from said first position to said second position.

18. The punch system of claim 17 further comprising a revision tibial tray trial comprising;

a stem;

a punch opening for receiving a punch; and a revision tray trial mating portion for receiving and locking with said connecting member of said alignment handle.

19. A punch system for preparing a tibial bone for a prosthetic implant, said punch system comprising:

a revision tibial tray trial comprising:

a stem;

a punch opening for receiving a punch;

a mating portion for receiving an alignment handle; and an alignment handle comprising:

a body having a connecting end portion, said connecting end portion comprising a locking member having at least one tab portion extending from said body and arranged to engage into an opening in said tray trail to prevent tray trail movement away from said body;

a connecting member located at said connecting end portion, said connecting member having a first position whereby said connecting member may be coupled with said mating portion of said tray trial; and a second position, whereby said connecting member is released from the mating portion of said tibial tray trial, wherein said connecting member is biased towards said first position; and a hand actuable quick-release button located on said body and coupled to said connecting member, said button actuable to move said connecting member from said first position to said second position.

20. The punch system of claim 19 wherein said connecting member comprises:

a sliding bolt extendable from said connecting end portion and retractable in a direction towards said body to said second position; and a spring, biasing said bolt towards said first position in a direction extending from said body.

* * * * *